United States Patent [19]

Wehling et al.

[11] Patent Number: 5,178,878

[45] Date of Patent: Jan. 12, 1993

[54] EFFERVESCENT DOSAGE FORM WITH MICROPARTICLES

[75] Inventors: Fred Wehling, New Hope; Steve Schuehle, Maple Grove; Navayanarao Madamala, Plymouth, all of Minn.

[73] Assignee: Cima Labs, Inc., Minneapolis, Minn.

[21] Appl. No.: 869,788

[22] Filed: Apr. 16, 1992

Related U.S. Application Data

[63] Continuation-in-part of Ser. No. 507,642, Apr. 11, 1990, abandoned, which is a continuation-in-part of Ser. No. 416,152, Oct. 2, 1989, abandoned.

[51] Int. Cl.⁵ .............................................. A61K 9/46
[52] U.S. Cl. .................................. 424/466; 424/44
[58] Field of Search .......................... 424/466, 44

[56] References Cited

U.S. PATENT DOCUMENTS

| | | | |
|---|---|---|---|
| 1,262,888 | 4/1918 | Westlake | 424/44 |
| 3,962,417 | 6/1976 | Howell | 424/52 |
| 4,613,497 | 9/1986 | Chaukin | 424/44 |
| 4,639,368 | 1/1987 | Niazi | 424/48 |
| 4,687,662 | 8/1987 | Schobel | 424/44 |
| 4,725,427 | 2/1988 | Ashmead | 424/44 |
| 4,753,792 | 6/1988 | Aberg | 424/44 |
| 4,940,588 | 7/1990 | Sparks | 424/490 |
| 5,055,306 | 2/1991 | Barry | 424/482 |

FOREIGN PATENT DOCUMENTS 0396335 11/1990 European Pat. Off.
0003160 10/1872 United Kingdom.

OTHER PUBLICATIONS

Pharmaceutical Dosage Forms-Tablets vol. 1, 2nd edition, Herbert A. Lieberman, ed pp. 372-376.

*Primary Examiner*—Thurman K. Page
*Assistant Examiner*—D. Gabrielle Phelan
*Attorney, Agent, or Firm*—Lerner, David, Littenberg, Krumholz & Mentlik

[57] ABSTRACT

A pharmaceutical dosage form incorporates microparticles which are susceptible to rupture upon chewing or which are adapted to provide substantially immediate release of the pharmaceutical ingredient contained in the microparticles. These microparticles are provided in a tablet with an effervescent disintegration agent. When the tablet is taken orally, the effervescent disintegration agent aids in rapid dissolution of the tablet and hence permits release of the microparticles, and swallowing of the microparticles, before the pharmaceutical ingredient is released from the microparticles. The system therefore provides particularly effective taste masking.

13 Claims, No Drawings

EFFERVESCENT DOSAGE FORM WITH MICROPARTICLES

The present application is a continuation-in-part of U.S. patent application No. 07/507,642, filed Apr. 11, 1990, now abandoned, which in turn is a continuation-in-part of U.S. patent application No. 07/416,152 filed Oct. 2, 1989, now abandoned, the disclosure of said earlier applications being hereby incorporated by reference herein.

BACKGROUND OF THE INVENTION

The present invention relates to the field of pharmaceutical orally ingested solid dosage forms.

One challenge in pharmacy is that many people are unwilling and/or unable to swallow tablets, capsules or other traditional solid dosage forms.

One approach suitable for persons who cannot or will not swallow a tablet or capsule is the use of effervescence.

Effervescence can be defined as the evolution of bubbles of gas in a liquid. As set forth in chapter 6 of *Pharmaceutical Dosage Forms: Tablets Volume I, Second Edition. A. Lieberman.* ed. 1989, Marcel Dekker, Inc. (the entirety of which is hereby incorporated by reference), effervescent mixtures have been known and used medicinally for many years. As discussed in this text, and as commonly employed, an effervescent tablet is dissolved in water to provide a carbonated or sparkling liquid drink. In such a drink the effervescence helps to mask the taste of medicaments. However, the use of effervescent tablets to prepare a beverage including medicaments, is not convenient. It requires prepatory steps before administration of the drug and also requires the presence of a suitable mixing container.

In a departure from the traditional use of effervescence, U.S. Pat. No. 4,639,368 describes a chewing gum containing a medicament capable of absorption through the buccal cavity and a composition capable of generating carbon dioxide as a taste masking agent. The gum may optionally include a further taste bud desensitizing compound. Unfortunately there are substantial disadvantages inherent in such a gum based delivery system. Many medicants are not suited for buccal absorption. Gums are difficult to prepare. Because of braces or other dental work, many persons are not permitted to chew gum. Furthermore, the medicament must be released into solution in the saliva. Thus the full taste of the medicament is perceived, subject only to the taste masking effect. If the flavor and/or the effervescent taste masker are insufficient and/or fade prior to the full release of medicament, the patient will be left with a gum having an objectionable taste. Gums also leave residues which must be disposed of.

Effervescent tablets have also been used in the dental area. Westlake, U.S. Pat. No. 1,262,888, Howell, U.S. Pat. No. 3,962,417 and Aberg U.S. Pat. No. 4,753,792 disclose effervescent dentifrice tablets adapted to foam in the mouth of a patient so as to provide a tooth cleansing action.

Chavkin U.S. Pat. No. 4,613,497 discloses a water foamable pharmaceutical composition incorporating an effervescent agent, a polysaccharide gum, and a gelling salt together with a pharmaceutically active ingredient. The composition is not intended to immediately disintegrate but rather to form a stable foam in the patient's stomach or other body cavity so that the active ingredient is gradually released from the foam. Sparks, U.S. Pat. No. 4,940,588 describes microparticles or "pharmasomes" which are adapted to provided "controlled release", i.e., a very slow release of the active ingredient from within the microparticles. These controlled-release particles are said to provide a "taste masking" action, and to resist degradation by chewing. However, such particles cannot be used where rapid dissolution of the drug is required.

Despite these and other efforts towards developments of suitable dosage forms, there have been unmet needs heretofore for improved dosage forms and for improved methods of administration of systematically distributable pharmaceutical ingredients such as drugs, vitamins and the like.

SUMMARY OF THE INVENTION

The present invention addresses these needs. One aspect of the present invention provides a solid pharmaceutical dosage form adapted for direct oral administration, i.e., for direct insertion into the mouth of a patient. A dosage form according to this aspect of the present invention includes a mixture incorporating at least one water and/or saliva activated effervescent disintegration agent and microparticles. The microparticles incorporate a pharmaceutical ingredient together with a protective material substantially encompassing the pharmaceutical ingredient. The term "substantially encompassing" as used in this context means that the protective material substantially shields the pharmaceutical ingredient from contact with the environment outside of the microparticle. Thus, each microparticle may incorporate a discrete mass of the pharmaceutical ingredient covered by a coating of the protective material, in which case the microparticle can be referred to as a "microcapsule". Alternatively or additionally, each microparticle may have the pharmaceutical ingredient dispersed or dissolved in a matrix of the protective material. The microparticles in each dosage form desirably contain an effective amount of at least one systematically distributable pharmaceutical ingredient. The mixture including the microparticles and effervescent agent desirably is present as a tablet of a size and shape adapted for direct oral administration to a patient, such as a human patient. The tablet is substantially completely disintegrable upon exposure to water and/or saliva. The effervescent disintegration agent is present in an amount effective to aid in disintegration of the tablet, and to provide a distinct sensation of effervescence when the tablet is placed in the mouth of a patient.

The effervescent sensation is not only pleasant to the patient but also tends to stimulate saliva production, thereby providing additional water to aid in further effervescent action. Thus, once the tablet is placed in the patient's mouth, it will disintegrate rapidly and substantially completely without any voluntary action by the patient. Even if the patient does not chew the tablet, disintegration will proceed rapidly. Upon disintegration of the tablet, the microparticles are released and can be swallowed as a slurry or suspension of the microparticles. The microparticles thus may be transferred to the patient's stomach for dissolution in the digestive tract and systemic distribution of the pharmaceutical ingredient.

The combination of the effervescent disintegration agent and the microparticles provides a uniquely effective dosage form for systemically distributable pharmaceutical ingredients which have unpleasant flavors or which should not be released within the mouth for other reasons. The microparticles may be relatively fragile microparticles susceptible to release of the pharmaceutical ingredient upon rupture of the microparticle. Because the tablet will disintegrate without chewing, the problem of microparticle rupture during chewing of the tablet is substantially eliminated. Stated another way, the effervescent action allows administration of the tablet without chewing, so as to maintain the efficacy of the protective material.

Moreover, the microparticles may be such as to provide rapid release of the pharmaceutical ingredient. Thus, the protective material and the physical characteristics of the microparticles may be such that the protective material does not greatly delay dispersion or dissolution of the pharmaceutical ingredient. As further discussed hereinbelow, the microcapsules may be such as to provide at least about 70 percent release within 30 minutes when tested according to standard test methods as discussed hereinbelow. A dosage form according to this aspect of the invention therefore will provide substantially prompt release of the pharmaceutical ingredient, as distinguished from a delayed or controlled release over a prolonged period of many hours. Such rapid release microparticles typically are relatively fragile and relatively prone to rupture and/or other types of pharmaceutical ingredient release in the patient's mouth. By themselves, such rapid release microparticles usually do not provide particularly effective masking of the taste of a pharmaceutical ingredient. However, according to this aspect of the present invention it has been found that combination of such rapid release microparticles with the other ingredients of the tablet, according to this aspect of the invention and particularly the effervescent disintegration agent, will indeed provide effective taste masking. This aspect of the invention thus provides a dosage form which offers both immediate release and effective taste masking.

Dosage forms according to the aspect of the present invention are particularly useful in administration of medications to individuals who cannot or will not chew, such as debilitated patients, patients who have difficulty swallowing solids, and the elderly.

The systemically distributable pharmaceutical ingredient may include at least one psychotropic drug such as a sedative, antidepressant, neuroleptic, or hypnotic. The present invention is especially valuable with psychotropic drugs in that a patient receiving such drugs, particularly a patient in a mental institution, often attempts to hold a conventional tablet or capsule concealed within his mouth rather than swallow it. The patient may then surreptitiously remove the tablet or capsule when medical personnel are not present. The preferred dosage forms according to this aspect of the present invention are substantially resistant to such concealment, inasmuch as they will disintegrate rapidly even if they are concealed within the mouth.

The present invention also encompasses methods of administering pharmaceutical ingredients to a patient. In a method according to this aspect of the present invention, a dosage form, such as the dosage forms described above, is provided to a patient and administered by placing the solid dosage form in the patient's mouth. Most preferably, the dosage form is substantially completely disintegrated in the patient's mouth by contact with the saliva. The effervescent disintegration ingredient provides a distinct effervescent sensation in the mouth, which stimulates salivation and thus further promotes the disintegration process. Most desirably, the disintegration process is conducted substantially without chewing or crushing of the tablet in the mouth. The microparticles are released from the tablet by such dissolution. Here again, the effervescent system reduces the need to chew, and protects the microparticles. This in turn provides effective masking of taste or other undesirable effects even with rupturable microparticles and/or rapidly-dissolving microparticles.

In methods according to this aspect of the present invention, the patient may be a person unwilling or unable to chew such as a recalcitrant or disabled patient, or an elderly patient. In a further aspect of the present invention particularly useful when administering a dosage form to a patient who seeks to defeat the administration by not swallowing the tablet, the administration is accompanied by observing the patient for a period of time sufficient for said tablet to completely disintegrate. By observation, the patient can be prevented from expelling the dosage form for sufficient time such that it may disintegrate.

DETAILED DESCRIPTION OF THE PREFERRED EMBODIMENTS

An oral dosage form according to one embodiment of the present invention is a tablet of a size and shape adapted for direct oral administration. The mass of each such tablet generally should be less than about 2.0 g and more preferably less than about 1.5 g. The tablet may include surface markings, cuttings, grooves, letters and or numerals for the purpose of decoration and/or identification. The tablet is, of course, in solid form. Preferably, the tablet is a compressed tablet. It includes microparticles containing one or more systemically distributable pharmaceutical ingredients, together with an effervescent disintegrating agent. The size of the tablet is also dependent upon the amount of material used. Circular, disk-like tablets desirably have diameters of about 11/16 inch or less, whereas elongated tablets desirably have a long dimension of about ⅞ inch or less.

The term "systemically distributable pharmaceutical ingredient" as used in this disclosure should be understood to mean a pharmaceutical ingredient which is conducted from the mouth to the digestive system for absorption through the stomach or intestines and systemic distribution through the bloodstream. The term is not intended to be limited to pharmaceutical ingredients which are systemically active or which systemically distribute over time. For the purposes of the present invention, a systemically distributable pharmaceutical ingredient may include pharmaceuticals or minerals, vitamins and dietary supplements. Mixtures of any of the foregoing are also contemplated by the term systemically distributable pharmaceutical ingredient.

By the term pharmaceutical(s) applicants mean a drug. Pharmaceutical(s) may include, without limitation, antacids, analgesics, anti-inflammatories, antibiotics, laxatives, anorexics, antiasthmatics, antidiuretics, antiflatuents, antimigraine agents, antispasmodics, sedatives, antihyperactives, tranquilizers, antihistamines, decongestants, betablockers, and combinations thereof.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyrdoxine, biotin, folic acid, vitamin $B_{12}$, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP) Coenzyme A (CoA) pyridoxal phosphate, biocytin, tetrahydrofolic acid, coenzyme $B_{12}$, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

The amount of systemically distributable pharmaceutical ingredient incorporated in each tablet may be selected according to known principles of pharmacy. An effective amount of systemically distributable pharmaceutical ingredient is specifically contemplated. By the term effective amount, it is understood that, with respect to for example pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The term effervescent disintegration agent(s) includes compounds which evolve gas. The preferred effervescent agents evolve gas by means of chemical reactions which take place upon exposure of the effervescent disintegration agent to water and/or to saliva in the mouth.

The bubble or gas generating reaction is most often the result of the reaction of a soluble acid source and an alkali metal carbonate or carbonate source. The reaction of these two general classes of compounds produces carbon dioxide gas upon contact with water included in saliva.

Such water activated materials must be kept in a generally anhydrous state with little or no absorbed moisture or in a stable hydrated form since exposure to water will prematurely disintegrate the tablet. The acid sources or acid may be any which are safe for human consumption and may generally include food acids, acid anhydrides and acid salts. Food acids include citric acid, tartaric acid, malic acid, fumaric acid, adipic acid, and succinic acids etc. Because these acids are directly ingested, their overall solubility in water is less important than it would be if the effervescent tablet formulations of the present invention were intended to be dissolved in a glass of water. Acid anhydrides and acid of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate.

The effervescent disintegration agent(s) of the present invention is not always based upon a reaction which forms carbon dioxide. Reactants which evolve oxygen or other gasses which are pediatrically safe are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

In general, the amount of effervescent disintegration agent of the present invention useful for the formation of tablets according to the present invention should range from about 5 to about 50% by weight of the final composition, and preferably between about 15 and about 30% by weight thereof. In a more preferred embodiment, the amount of effervescent disintegration agent according to the present invention ranges from between about 20 and about 25% by weight of the total composition.

More specifically, tablets according to the present invention should contain an amount of effervescent disintegration agent effective to aid in the rapid and complete disintegration of the tablet when orally administered. By "rapid", it is understood that the tablets of the present invention should disintegrate in the mouth of a patient in less than 10 minutes, and desirably between about 30 seconds and about 7 minutes. In a particularly preferred embodiment according to the present invention, the tablet should dissolve in the mouth in between about 30 seconds and about 5 minutes. Disintegration time in the mouth can be measured by observing the disintegration time of the tablet in water at about 37° C. The tablet is immersed in the water without forcible agitation. The disintegration time is the time from immersion for substantially complete dispersion of the tablet as determined by visual observation. As further discussed below, tablets according to the preferred embodiments of the invention include microparticles or other discrete inclusions. These typically are more slowly soluble than the tablet binder. As used in this disclosure the term "complete disintegration" of the tablet does not require dissolution or disintegration of such microcapsules or other discrete inclusions. Disintegration times referred to in this disclosure should be understood as determined by this method unless otherwise specified.

Also, the amount of effervescent disintegration agent present in the tablet should be effective to provide an effervescent sensation in the mouth of the patient who consumes the tablet. Thus, the patient should be able to perceive a distinct sensation of "fizzing" or bubbling as the tablet disintegrates in the mouth. To provide this sensation, the amount of effervescent agent in each tablet desirably is arranged to provide about 20 to about 60 $cm^3$ of gas. The "fizzing" sensation substantially enhances the organoleptic effects of the tablet. Thus, the amount of effervescent disintegration agent useful in accordance with the present invention is also an amount effective to provide a positive organoleptic sensation to a patient. A "positive" organoleptic sensation is one which is pleasant or enjoyable and which can be perceived readily by a normal human being.

It should also be noted that the hardness of a tablet may also play a role in disintegration time. Specifically, increasing the hardness of a tablet may increase the disintegration time just as decreasing hardness may decrease disintegration time.

The dosage form according to this aspect of the present invention may further include one or more additional adjuvants which can be chosen from those known in the art including flavors, dilutents, colors, binders, filler, compaction vehicles, and non-effervescent disintegrants.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Non-effervescent disintegrants include starches as corn starch, potato starch and modified starches thereof, sweeteners, clays, such as bentonite, microcrystalline cellulose, alginates, gums such as agar, guar, locust bean, karaya, pecitin and tragacanth. Disintegrants may comprise up to about 20 weight percent and preferably between about 2 and about 10 percent of the total weight of the composition.

Coloring agents may include titanium dioxide, and dyes suitable for food such as those known as F.D. & C. dyes and natural coloring agents such as grape skin extract, beet red powder, beta-carotene, annato, carmine, turmeric, paprika, etc.. The amount of coloring used may range from about 0.1 to about 3.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.5 to about 3.0 by weight based upon the weight of the composition. Particularly preferred flavors are the grape and cherry flavors and citrus flavors such as orange.

Tablets according to this aspect of the present invention can be manufactured by well-known tableting procedures. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minute can be produced in this fashion. Various tableting methods, well known to those skilled in the art, are comprehensively discussed throughout the aforementioned Lieberman text.

Materials to be incorporated in the tablets, other than the microparticles and the effervescent disintegration agent, may be pretreated to form granules that readily lend themselves to tableting. This process is known as granulation. As commonly defined, "granulation" is any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation.

As noted in Chapter 6 of *Pharmaceutical Dosage Forms*, supra, lubricants normally are used in manufacture of effervescent tablets. Without the use of an effective lubricant, tableting by use of high speed equipment would be difficult. Effervescent granulations are inherently difficult to lubricate due to both the nature of the raw materials and the requirement that the tablets disintegrate rapidly.

Lubricant, as used herein, means a material which can reduce the friction arising at the interface of the tablet and the die wall during compression and ejection thereof. Lubricants may also serve to prevent sticking to the punch and, to a lesser extent, the die wall as well. The term "antiadherents" is sometimes used to refer specifically to substances which function during ejection. As used in the present disclosure, however, the term "lubricant" is used generically and includes "antiadherents". Tablet sticking during formation and/or ejection may pose serious production problems such as reduced efficiency, irregularly formed tablets, and non-uniform distribution of intended agents or ingredients to be delivered thereby. These problems are particularly severe with high speed tableting approaches and methods.

Lubricants may be intrinsic or extrinsic. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity.

Intrinsic lubricants are incorporated in the material to be tableted. Magnesium, calcium and zinc salts of stearic acid have long been regarded as the most efficient intrinsic lubricants in common use. Concentrations of one percent or less are usually effective.

Other traditional intrinsic lubricants include hydrogenated and partially hydrogenated vegetable oils, animal fats, polyethyleneglycol, polyoxyethylene monostearate, talc, light mineral oils, sodium benzoate, sodium lauryl sulphate, magnesium oxide and the like. See European Patent Application No. 0,275,834, the disclosure of which is incorporated by reference. See also Leal, et al., U.S. Pat. No. 3,042,531.

Lubricants, according to the present invention, may be used in an amount of up to 1.5 weight percent and preferably between about 0.5 and about 1.0 weight percent of the total composition.

Intrinsic lubricants pose certain serious difficulties when used in conventional tablets. Many lubricants materially retard the disintegration of non-effervescent tablets. However, the effervescent disintegration agents used in the dosage form of the present invention overcome any such retardation. In dissolution of conventional effervescent tablets, the lubricant may cause "scumming" and/or agglomeration. Stearates, for example leave an objectionable "scum" when an effervescent tablet is placed in a glass of water. This "scum" reduces the aesthetic appeal of the solution made from an effervescent dosage form. However, because the tablets of the present invention dissolve in the mouth, the solution is never seen by the user. Therefore, the propensity of a lubricant to "scum" is unimportant. Thus, lubricants which can cause dissolution or scumming problems in other dosage forms can be used in dosage forms according to the present invention without material adverse effect.

A pharmaceutical ingredient is present in microparticles. Each microparticle incorporates the pharmaceutical ingredient in conjunction with a protective material. The microparticle may be provided as a microcapsule or as a matrix-type microparticle. Microcapsules typically incorporate a discrete mass of the pharmaceutical ingredient surrounded by a discrete, separately observable coating of the protective material. Conversely, in a matrix-type particle, the pharmaceutical ingredient is dissolved, suspended or otherwise dispersed throughout the protective material. Certain microparticles may include attributes of both microcapsules and matrix-type particle. For example, a microparticle may incorporate a core incorporating a dispersion of the pharmaceutical ingredient in a first protective material and a coating of a second protective material, which may be the same as or different from the first protective material surrounding the core. Alternatively, a microparticle may incorporate a core consisting essentially of the pharmaceutical ingredient and a coating incorporating the protective material, the coating itself having some of the pharmaceutical ingredient dispersed within it. These and other known microparticle configurations may be employed.

The microparticles desirably are between about 75 and 600 microns mean outside diameter, and more preferably between about 150 and about 500 microns. Microparticles above about 200 microns may be used. Thus, the microparticles may be between about 200 mesh and about 30 mesh U.S. standard size, and more preferably between about 100 mesh and about 35 mesh.

The microparticles may be susceptible to release of the pharmaceutical ingredient upon rupture of the microparticle. Where the pharmaceutical ingredient has a perceptible taste, susceptibility of the microparticles to rupture can be measured, on a practical basis, by subjecting the microparticles to a chewing test. If the taste of the pharmaceutical ingredient can be observed by a normal observer after chewing a reasonable portion of such microparticle, such as approximately 250 milligrams thereof, for about 30 seconds, then the microparticles can be considered susceptible to release of the pharmaceutical ingredient upon rupture. An alternative test may be performed by subjecting the microparticles to the physical forces encountered in a tableting press and determining whether or not the propensity of the microparticles to release the pharmaceutical ingredient has increased. One practical test using that approach is to make a tableting mixture using the following ingredients:

TABLE I

| Ingredient | Mg/Tablet |
|---|---|
| Mannitol | 225.0 mg |
| Magnesium Stearate | 5.0 mg |
| Silicon Dioxide | 1.0 mg |
| Microparticles | 90-100 mg |

That tableting mixture is then tableted in a conventional tableting press to a relatively low hardness value, preferably about 1.5 kilo pounds and, separately, to a higher hardness value of about 4 kilo pounds. These tablets are then compared to determine whether the harder tablet has a greater propensity to release the pharmaceutical ingredient. Where the pharmaceutical ingredient has a significant taste, the comparison can be made by placing the tablets on the tongue in separate trials and allowing the tablet to dissolve without chewing. If the harder tablet (4 kilo pounds) provides a stronger taste, then the microparticles can be considered susceptible to rupture.

Preferably, the microparticles provide at least about 70 percent release within about 30 minutes when tested using USP XXII apparatus 2 at 50 rpm using 50-250 mg microparticles and 900 ml water. The percentage release in this case is the percent of the pharmaceutical ingredient dissolved in the water as a percent of the pharmaceutical ingredient present in the original charge of microcapsules. Ordinarily, the percentage release does not vary appreciably with the amount of microparticles used for the test, within the range noted above. If there is any such variation, however, the percentage release using 150 mg particles can be taken as definitive. The term "release" as used in this disclosure with reference to microparticles should be understood as measured according to this test method. Still higher release values, such as about 75 percent or more after the dissolution for 30 minutes using the aforementioned conditions, or, even more preferably, at least about 80 percent upon dissolution under such conditions, are even more preferred. Microparticles meeting these specifications can be said to provide substantially prompt release of the pharmaceutical ingredient. Although such prompt release is preferred, the protective material utilized in the microparticle desirably should not dissolve instantaneously in water or saliva. That is, the microparticle should resist dissolution and release for a period of time, typically a few seconds or so, sufficient to permit the patient to swallow the released microcapsules as the tablet disintegrates. Microparticles made using any of the polymeric protective materials discussed below will not dissolve instantaneously.

Ingredients and methods for making microparticles are well-known in the art. Methods of microencapsulation, for example, are described in the aforementioned Lieberman text, *Pharmaceutical Dosage Form: Tablets Volume 1*, Second Edition, New York, 1989, at pages 372–376. That disclosure is hereby incorporated by reference herein. One method taught in Lieberman is the technique of phase separation or coacervation which involves processing three mutually immiscible phases, one containing the pharmaceutical ingredient, another containing the protective coating material and a third containing a liquid vehicle used only in the manufacturing phase. The three phases are mixed and the protective material phase deposits by absorption on the pharmaceutical ingredient phase. After this step, the protective material phase is converted to a substantially solid form by cross-linking or by removal of solvent from this phase. Other common techniques may be used for forming matrix-type microparticles wherein the pharmaceutical ingredient is dispersed in the protective material. For example, the pharmaceutical ingredient and a solution of a polymeric protective material may be sprayed to form droplets and contacted with a gas such as hot air so as to remove the solvent from the droplets. Such a mixture may also be dried to a solid and then comminuted to form the microparticles. Alternatively, the mixture of the pharmaceutical ingredient and polymeric solution may be mixed with an immiscible liquid phase and the solvent may be removed through this phase. The mixing step may include emulsification of the phase bearing the pharmaceutical ingredient and the protective material in the immiscible liquid phase.

The protective material may incorporate polymers such as those conventionally utilized in protective materials for microparticles. A wide variety of polymers are known for this purpose. Any such known polymeric material, utilized heretofore in production of microcapsules and/or matrix-type microparticles may be employed as a protective material in microparticles according to the present invention. Among these are cellulosic materials such as naturally occurring cellulose and synthetic cellulose derivatives; acrylic polymers and vinyl polymers. Other suitable polymers include proteinaceous materials such as gelatin, polypeptides and natural and synthetic shellacs and waxes. Particularly preferred protective material polymers include ethylcellulose, methylcellulose, carboxymethylcellulose and the acrylic resin materials sold under the registered trademark EUDRAGIT by Rhone Pharma GmbH of Weiterstadt, Germany.

Many of the protective material polymers discussed above have substantial resistance to dissolution in water. Such water-insoluble materials can be used to make delayed-release microparticles. Preferably, however, where the protective material incorporates water-insoluble materials of this nature, it also includes other ingredients to promote more rapid release of the pharmaceutical ingredient. Such release promoters include soluble polymers and, in particular, polyfractional alcohols such as mannitol, as well as magnesium oxide. For example, the acrylic material of the type known as EUDRAGIT® RL30-D, when used with conventional coingredients such as methylcellulose and magnesium sterate tends to provide a slow release, typically about 50 percent or less after 30 minutes. However, a protective material incorporating the same polymeric material in conjunction with about 2 to about 4, and preferably about 2.7 parts mannitol per part EUDRAGIT material on a solids basis, and also incorporating about 0.05 to about 0.2, and preferably about 0.09 parts magnesium oxide per part EUDRAGIT solids provides a protective material with substantially immediate release properties. Blends of acrylic polymers such as EUDRAGIT with polyfunctional alcohol such as mannitol, and, desirably, with oxides of alkaline earth metals such as magnesium oxide provide prompt release of the pharmaceutical ingredient. Such blends do not include the plasticizers commonly used with acrylic protective materials. Microparticles using such blends normally are susceptible to release upon chewing, but nonetheless provide excellent taste-masking properties in tablets according to this invention.

The foregoing will be better understood with reference to the following examples which detail certain procedures for the manufacture of tablets according to the present invention. All references made to these examples are for the purposes of illustration. They are not to be considered limiting as to the scope and nature of the present invention.

EXAMPLE I

The following ingredients are employed to form microparticles:

TABLE II

| Ingredient | Grams Solids | % By Weight |
|---|---|---|
| EUDRAGIT RL-30-D | 157.5 | 23.8 |
| Pseudoephedrine HCl | 70.0 | 10.6 |
| Mannitol | 420.0 | 63.5 |
| Magnesium Oxide | 14.0 | 2.1 |

The EUDRAGIT material is furnished by the manufacturer as a dispersion containing 30% solids (polymer) in water. The quantity need to provide 157.5 grams solids is placed in a beaker and mixed to form a vortex. The mannitol and pseudoephedrine HCl are added and mixing is continued for 10 minutes. After this 10 minute mixing period, the magnesium oxide is added and mixing is continued for another 10 minutes. These mixing steps take place at room temperature. The resulting mixture is poured into a tray and dried in an oven at 50° C. under air for 1 hour. After 1 hour, the resulting partially dried mixture is broken into lumps and then dried for an additional hour at 50° C. The dried lumps are then comminuted to microparticles, and screened through an 8 mesh screen. The screened microparticles are dried for an additional hour at 60° C.

The fraction of the resulting microparticles passing through a 30 mesh screen is collected. These microparticles provide in excess of 90 percent release of the pseudoephedrine HCl pharmaceutical ingredient after 30 minutes. When tableted into a conventional chewable tablet and chewed, these microparticles rupture and substantially release the pseudoephedrine so that the characteristic bitter taste of this material is quite evident.

A portion of the microparticles are tableted into an effervescent tablet of about 1.0–2.0 kilo pounds hardness with an effervescent disintegration agent and other ingredients according to the following recipe:

| Ingredient | Mg/Tablet |
| --- | --- |
| Mannitol | 225.0 mg |
| Aspartame | 40.0 mg |
| Cherry Flavor | 6.0 mg |
| Magnesium Stearate | 5.0 mg |
| Silicon Dioxide | 1.0 mg |
| Sodium Bicarbonate | 100.0 mg |
| Citric Acid | 80.0 mg |
| Microparticles | 94.3 mg |

The effervescent tablet has a dissolution time of less than about 1.0 minutes. When administered by mouth, it provides substantially prompt bioavailability of the pseudoephedrine.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

What is claimed is:

1. A solid pharmaceutical dosage form adapted for direct oral administration to a human comprising: a mixture of at least one saliva activated effervescent agent and a plurality of microparticles, each said microparticle including at least one systemically distributable pharmaceutical ingredient and a protective material substantially encompassing said pharmaceutical ingredient, said microparticles having at least about 70 percent 30-minute release, said mixture being present as a tablet of a size and shape adapted for direct oral administration to a human patient, said tablet being substantially completely disintegrable so as to release said microparticles upon exposure to saliva, said at least one effervescent agent being present in an amount which is effective to aid in rapid disintegration of said tablet, without chewing, and thereby release said microparticles.

2. A solid pharmaceutical dosage form adapted for direct oral administration to a human comprising: a mixture of at least one saliva activated effervescent agent and a plurality of microparticles, each said microparticle including at least one systemically distributable pharmaceutical ingredient and a protective material substantially encompassing said pharmaceutical ingredient, said microparticles being susceptible to release of said pharmaceutical ingredient upon rupture thereof, said mixture being present as a tablet of a size and shape adapted for direct oral administration to a human patient, said tablet being substantially completely disintegrable so as to release said microparticles upon exposure to saliva, said at least one effervescent agent being present in an amount which is effective to aid in rapid disintegration of said tablet, without chewing, and thereby release said microparticles.

3. A dosage form as claimed in claim 1 wherein each said microparticle includes said pharmaceutical ingredient dispersed in a matrix of said protective material.

4. A dosage form as claimed in claim 1 wherein said microparticles have a mean diameter about 200 microns.

5. A dosage form as claimed in claim 1 wherein said microparticles consist essentially of particles between about 200 mesh and about 30 mesh.

6. A dosage form as claimed in claim 1 wherein said at least one systemically distributable pharmaceutical ingredient includes at least one psychotropic drug.

7. A dosage form as claimed in claim 2 wherein each said microparticle includes said pharmaceutical ingredient dispersed in a matrix of said protective material.

8. A dosage form as claimed in claim 2 wherein said microparticles have a mean diameter about 200 microns.

9. A dosage form as claimed in claim 2 wherein said microparticles consist essentially of particles between about 200 mesh and about 30 mesh.

10. A dosage form as claimed in claim 2 wherein said at least one systemically distributable pharmaceutical ingredient includes at least one psychotropic drug.

11. A dosage form as claimed in claim 1 wherein said microparticles are susceptible to release of said pharmaceutical ingredient upon rupture thereof.

12. A method of administering at least one systemically distributable pharmaceutical ingredient to a human patient comprising the steps of:
a) providing a tablet including a mixture of at least one saliva activated effervescent agent and microparticles incorporating said pharmaceutical ingredient and a protective material substantially encompassing said pharmaceutical ingredient, said microparticles having at least about 70 percent 30-minute release, said tablet being substantially completely disintegrable upon exposure to saliva, said at least one effervescent agent being present in an amount which is effective to aid in rapid disintegration of said tablet, without chewing; and
b) placing said tablet in the mouth of a patient so that saliva in said patient's mouth activates said effervescent agent in said tablet and said tablet substantially completely disintegrates in the patient's mouth to release said microparticles, said at least one effervescent agent promoting disintegration of said tablet and providing a distinct sensation of effervescence during said disintegration, whereby said sensation of effervescence will substantially promote secretion of saliva by the patient to thereby further promote said disintegration.

13. A method of administering at least one systemically distributable pharmaceutical ingredient to a human patient:
a) providing a tablet including a mixture of at least one saliva activated effervescent agent and microparticles incorporating said pharmaceutical ingredient and a protective material substantially encompassing said pharmaceutical ingredient, said microparticles being susceptible to release of said pharmaceutical ingredient upon rupture thereof, said tablet being substantially completely disintegrable upon exposure to saliva, said at least one effervescent agent being present in an amount which is effective to aid in rapid disintegration of said tablet, without chewing; and
b) placing said tablet in the mouth of a patient so that saliva in said patient's mouth activates said effervescent agent in said tablet and said tablet substantially completely disintegrates in the patient's mouth, said at least one effervescent agent promoting disintegration of said tablet and providing a distinct sensation of effervescence during said disintegration, whereby said sensation of effervescence will substantially promote secretion of saliva by the patient to thereby further promote said disintegration and minimize any need for chewing to promote said disintegration, said microparticles being released from said tablet upon disintegration of the tablet in said patient's mouth.

* * * * *